United States Patent [19]
Wheeler

[11] Patent Number: 6,022,874
[45] Date of Patent: *Feb. 8, 2000

[54] PIPERAZINE BASED CYTOFECTINS

[75] Inventor: Carl J. Wheeler, Poway, Calif.

[73] Assignee: Vical Incorporated, San Diego, Calif.

[*] Notice: This patent is subject to a terminal disclaimer.

[21] Appl. No.: 09/219,758

[22] Filed: Dec. 23, 1998

Related U.S. Application Data

[63] Continuation of application No. 08/726,348, Oct. 3, 1996, Pat. No. 5,861,397.

[51] Int. Cl.$^7$ .......................... A01N 43/58; A01N 25/26; A61K 39/00
[52] U.S. Cl. .......................... 514/247; 514/247; 514/255; 424/1.21; 424/417; 424/420; 424/812; 424/9.321; 427/2.14; 544/358; 544/359
[58] Field of Search ................... 514/247, 255; 424/1.21, 9.321, 417, 420, 812; 427/2.14; 544/358, 359

[56] References Cited

U.S. PATENT DOCUMENTS

| | | | |
|---|---|---|---|
| 2,368,208 | 1/1945 | Epstein | 554/106 |
| 3,265,719 | 8/1966 | Cowen et al. | 554/110 |
| 4,864,060 | 9/1989 | Karalis et al. | 564/292 |
| 5,049,386 | 9/1991 | Eppstein et al. | 424/427 |
| 5,068,431 | 11/1991 | Karalis et al. | 564/301 |
| 5,144,060 | 9/1992 | Morita et al. | 560/170 |
| 5,264,618 | 11/1993 | Felgner et al. | 560/224 |
| 5,279,833 | 1/1994 | Rose | 424/450 |
| 5,334,761 | 8/1994 | Gebeyehu et al. | 564/197 |
| 5,861,397 | 1/1999 | Wheeler | 514/247 |

FOREIGN PATENT DOCUMENTS

| | | |
|---|---|---|
| PCT/US94/13362 | 11/1994 | WIPO . |
| PCT/US94/13428 | 11/1994 | WIPO . |
| WO 95/14381 | 6/1995 | WIPO . |
| WO 95/14651 | 6/1995 | WIPO . |

OTHER PUBLICATIONS

Solodin, Igor and Heath, *Synlett*, p. 619, Jul. 1996 (received for publication Oct. 11, 1995). "Synthesis of Amphiphilic Piperidinium Derivatives. Cationic Lipids $4^1$."

Solodin, et al., *Synlett*, p. 620, Jul. 1996 (received for publication Oct. 11, 1995). "Synthesis of Amphiphilic Derivatives of N–Methyldiethanolamine. Cationic Lipids $5^1$."

Solodin, Igor and Heath, *Synlett*, p. 617–618, Jul. 1996 (received for publication Sep. 19, 1995). "Synthesis of Novel Cationic Lipids with a Guanidine Group. Cationic Lipids $3^1$."

Nabel et al., *Human Gene Therapy*, 3:399–410, 1992. "Immunotherapy of Malignancy by in VivoGene Transfer into Tumors."

Rosenthal et al., *The Journal of Biological Chemistry*, 235(8), 1960 "A Synthetic Inhibitor of Venom Lecithinase A*."

Felgner et al., *Proc. Natal. Acad. Sci*, USA, 84:7413–7417, 1987. "Lipofection: A Highly Efficient, Lipid–Mediated DNA–Transfection Procedure."

Felgner et al., *The Journal of Biological Chemistry*, 269: 2550–2561, 1994. "Enhanced Gene Delivery and Mechanism Studies with a Novel Series of Cationic Lipid Formulations*."

Wheeler et al., *BBA*, 1280: 1–11, 1996. "Converting an Alcohol to an Amine in a Cationic . . . Ultrastructure of DNA–Cytofectin Complexes."

*Primary Examiner*—John L. LeGuyader
*Assistant Examiner*—Janet L. Epps
*Attorney, Agent, or Firm*—Knobbe Martens Olson & Bear, LLP

[57] ABSTRACT

The present invention relates to piperazine based amphilic cationic lipids useful for gene therapy, transfection, and introducing immunogenic compounds for the purpose of vaccination. The disclosed compounds have lipophilic moieties linked to the ring nitrogens. In addition, at least one of the ring nitrogens is quatranized and linked to a hydrocarbon having at least one heteroatom.

22 Claims, 8 Drawing Sheets

*IN VITRO* ACTIVITY OF HEMOE-BP

GENERAL STRUCTURE

HE-MOE-BP   R=C14, n=2, X=OH
GA-MOE-BP   R=C14, n=3, X=NH2
HE-LOE-BP   R=C12, n=2, X=OH
GA-LOE-BP   R=C14, n=3, X=NH2
BA-LOE-BP   R=C12, n=4, X=NH2

PIPERAZINE BASED CYTOFECTINS

RELATED APPLICATIONS

The present application is a continuation of U.S. patent application Ser. No. 08/726,348 filed Oct. 3, 1996, now U.S. Pat. No. 5,861,397, the disclosure of which is incorporated herein by reference in its entirety.

BACKGROUND OF THE INVENTION

The present invention relates to complex amphiphilic lipids. It relates particularly to complex cationic amphiphilic lipids comprising a piperazine ring having a hydrocarbon chain including at least one heteroatom joined to at least one of the nitrogens in the ring and lipophilic moieties attached to the ring nitrogens.

BACKGROUND OF THE INVENTION

Amphiphilic molecules may be used to intracellularly deliver therapeutic or bioactive molecules into the cell. For example, WO 95/14381 discloses the use of amphiphilic guanidine derivatives for intracellular delivery of macromolecules. Cationic lipids are amphiphilic molecules having a lipophilic region, commonly comprising one or more hydrocarbon or alkyl groups, and a hydrophilic region comprising at least one positively charged polar head group. Cationic lipids are useful for facilitating the transport of macromolecules through the plasma membrane of cells and into the cytoplasm. The process, which can be carried out in vivo as well as in vitro, is known as transfection, and the cationic lipids used in such techniques are known as cytofectins.

Cytofectins which enhance transfection efficiency to a statistically significant extent are beneficial. As little as a two fold increase over the activity obtained with naked DNA is beneficial, although preferably transfection efficiency is increased 5–10 fold, and more preferably transfection efficiency is enhanced more than 10 fold.

Typically, cytofectins are combined with a neutral zwitterionic lipid such as a phospholipid, because it has been found that the two amphiphilic lipid species in combination are able to form vesicles comprising ordered lipid bilayers that are more effective at transfection than the cytofectin alone. These vesicles, or liposomes, have multiple positive charges on the surface which allow them to form a complex with a polynucleotide or other anionic molecule such as negatively charged proteins. Remaining net cationic charges on the surface of the polynucleotide/cytofectin/neutral lipid complex are capable of strong interaction with the predominantly negative charge of the cell membrane surface.

Apart from the basic features of amphiphilic properties and the polar head group, cytofectins have considerable structural diversity in the lipophilic and hydrophilic regions. Many different cytofectin species have been synthesized for use in transfection and are now commercially available. Such cytofectins include, for example, LIPOFECTIN® (a 1:1 w/w liposome formulation of the cationic lipid N-[1-(2,3-dioleyloxy)propyl]-N,N,N-trimethylammonium chloride (DOTMA) and dioleolyl phosphatidylethanolamine (DOPE) in membrane filtered water), LIPOFECTACE™ (a 1:2.5 w/w liposome formulation of the cationic lipid dimethyl dioctadecylammonium bromide (DDAB) and dioleoyl phosphatidylethanolamine (DOPE)), LIPOFECTAMINE™ (a 3:1 w/w formulation of the polycationic lipid 2,3-dioleyloxy-N-[2(sperminecarboxamido)ethyl]-N,N-dimethyl-1-propanaminiumtrifluoracetate (DOSPA) Chemical Abstracts name: N-[2({2,5-bis(3-aminopropyl)amino]-1-oxypentyl}amino)ethyl]-N-N-dimethyl-2-3-bis(9-octadecenyloxy)-1-propanaminium trifluoroacetate) and the neutral lipid dioleolyphosphatidylethanolamine (DOPE) in membrane filtered water), TRANSFECTAM® (dioctadecylamidoglycylspermine), and DOTAP™ (N-[1-92,3-dioleoyloxy)propyl]-N,N,N-trimethylammonium methylsulfate). The structural diversity of effective cytofectins reflects, in part, the observation that structure-function-recognition aspects of cytofectins differ with respect to distinct applications in cells. Experience with cytofectins structurally similar to the DOTMA compounds indicates that transfection activity depends in part on the cell type transfected (Felgner et al. *J. Biol. Chem.* 84:7413–7417, 1987; Wheeler et al. Biochem. Biophys. Acta, 1280:1–11 (1996)). Particularly, cationic lipids having a spermine substitution of the ammonium groups proved more effective than DOTMA for transfection of some cell lines. This phenomenon suggests that effective transfection depends not only on passive fusion of the cationic lipid complex with the structural lipid bilayer of the plasma membrane, but on specific cellular characteristics and interaction between cell components and the individual cationic lipid species.

Structural variants among cytofectin species are therefore an indication of a more sophisticated understanding of the multiple and complex interactions of cytofectins with cells, and an effort on the part of investigators to take advantage of one or more of these interactions.

DOTMA, N-[1-(2,3-dioleyloxy)propyl]-N,N,N-trimethyl ammonium, disclosed in U.S. Pat. No. 5,049,386 to Epstein, was one of the first cationic lipids developed, and lipids of this group have become reference compounds in evaluating comparative cytofectin potency in the development of new structural variants. DOTMA lipids are characterized by a propanaminium group having a quaternary nitrogen, which provides the cationic site of the molecule, together with a pair of $C_{18}$ hydrocarbons that are ether-linked to the propyl backbone of the molecule. The quaternary nitrogen is trisubstituted with relatively shorter alkyl chains, such as methyl groups. A structurally similar cationic lipid, 1,2-bis(oleoyloxy)-3-3-(trimethylammonia)propane (DOTAP), comprises acyl, rather than ether-linked alkyl groups, and is believed to be more easily metabolized by target cells.

Some species of cationic lipids, for example, ammonium salts directly substituted by alkyl or acyl groups, were developed primarily for purposes of economy (U.S. Pat. No. 5,279,833 to Rose). Others were developed in an effort to provide less toxic effects; for example, a highly biocompatible cytofectin prepared from phosphatidylcholine and sphingomyelin: 1, 2-dioleoyl-sn-glycero-3-ethylphosphocholine (Avanti Polar Lipids, Inc. Alabaster, Ala., Cat. Nos. 890700-706).

U.S. Pat. No. 5,264,618 to Felgner et al. discloses cytofectins that are structurally similar to the Rosenthal Inhibitor (RI) of phospholipase A (Rosenthal et al., *J. Biol. Chem.* 235:2202–2206 (1960)) and diacyl- or alkyl/acyl-species thereof. Rosenthal Inhibitor based cytofectins are characterized by having a substituent with the structure linked to a quaternary nitrogen.

The RI based series of compounds are known by acronyms having the pattern: DORIE ($C_{18}$); DPRIE ($C_{16}$); and DMRIE ($C_{14}$). These acronyms imply a common basic chemical structure; for example, DMRIE (dimyristoyl Rosenthal inhibitor ether) is 1-propanaminium, N-(2-hydroxyethyl)-N,N-dimethyl-2,3-bis(tetradecyloxy)-, bromide, (±)—(CAS registry:146659); the others differ in their substituent alkyl groups. These cytofectins, having a polar hydroxyethyl substituent on the quaternary ammonium group, provide more effective transfection in many cases than DOTMA type compounds. A study of the effect of varying substituents at the hydroxyalkyl moiety and variation of alkyl chain lengths on the transfection efficacy of the RI cytofectins is presented in Felgner et al. (*J. Biol. Chem.* 269:2550–2561, 1994). Again, the studies showed that the optimum hydroxyl alkyl chain length is cell-type dependent.

The conversion of DMRIE to βAE-DMRIE (Wheeler et al., 1280 Biochem. Biophys. Acta: 1–11 (1996)) has been found to have a significant effect on cytofectin activity. DMRIE, which has a quaternary nitrogen adjacent to a primary alcohol, thus imparting a pH independent positive charge, is one of the most active cytofectins now known. However, the substitution of a primary amine group for the alcohol on DMRIE to give βAE-DMRIE was found to form DNA complexes that are structurally distinct from those with DMRIE, and βAE-DMRIE is able to transfect many cell lines effectively in the absence of helper co-lipids. The observation that a single substitution in the cytofectin skeleton can provide marked changes in transfection properties suggests that other modifications can bring about similar improvements in gene delivery.

Continuing studies of the transfection event indicate that cationic lipids may facilitate not only entry of the functional molecule into the cytoplasm of a cell, but may also provide additional beneficial capabilities; for example, protecting the functional molecule from lysosomal degradation, facilitating entry into the nuclear compartment, or even preventing the degradation of the RNA transcription product by cytoplasmic enzymes. These functions of cationic molecules are believed to be related to specific structural features. Accordingly, there is a need for cytofectins that are particularly suited to transfection of foreign molecules into specific cell types. There is also a need to develop cytofectins that are able to perform specific intracellular functions.

WO 95/14651 discloses piperazine based cytofectins in which lipophilic hydrocarbon chains are ether or ester linked to each of the nitrogens through a short hydrocarbon linker. Additionally, at least one of the nitrogens is also linked to a lower alkyl group such that the nitrogen is positively charged. However, the lower alkyl groups linked to the cytofectins disclosed in WO 95/14651 do not permit the attachment of additional bioactive groups to the cytofectin, thereby restricting the bioactive groups that can be delivered to those which are not covalently attached to the cytofectin. Thus, there exists a need for cytofectins capable of delivering a covalently linked bioactive group. Additionally, a need exists for piperazine based cytofectins having improved transfection efficiencies.

SUMMARY OF THE INVENTION

The present invention relates to piperazine based cytofectins of the following structure:

wherein
$R_1$, $R_2$ and $R_4$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups each of which may contain 0–5 heteroatoms;

$R_3$ is absent, H, $R_1$ as defined above, or an amino acid, peptide, polypeptide, protein, nucleic acid, nucleotide or nucleoside, polynucleotide, polynucleoside, mono-, di- or polysacchararide, or other bioactive or pharmaceutical agent or the following structure:

wherein $R_7$ through $R_{12}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or $CR_1$;
T is O, N, S, Se, or C;
A is O, N, S, Se, or C;
$Y_1$ and $Y_2$ are independently absent, O, N, NH, S, or Se;
$X_1$ is absent, O, N, NH, S, or Se;
m and p are independently 0–6;
W is a pharmaceutically acceptable anion; and
wherein $R_2$—$X_1$—$R_3$ is not a lower alkyl of up to 6 carbons inclusive.

In a preferred embodiment of the cytofectins of the structure above, m and p are 2. In a more highly preferred aspect of this embodiment, $Y_1$ and $Y_2$ are O. In a highly preferred embodiment, $R_1$ and $R_4$ are selected from the group consisting of $C_{10}H_{21}$, $C_{12}H_{25}$, and $C_{14}H_{29}$. In yet a further preferred embodiment, $R_2$ is selected from the group consisting of absent, $CH_2$, $(CH_2)_2$, $(CH_2)_3$, $(CH_2)_4$, $(CH_2)_5$, $(CH_2)_6$ and CO—CH—$NH_2$. Preferentially, $X_1$ is selected from the group consisting of absent, NH and O.

In additional preferred aspects of the above embodiment, $X_1$ is NH and $R_3$ is selected from the group consisting of H, CO—NH—$CH_3$, and CO—$CH_2$—$NH_2$. In another preferred aspect of the above embodiment, $X_1$ is O and $R_3$ is H.

In a further preferred aspect of the above embodiment, $X_1$ is absent and $R_3$ is $CH_2$—$CH_2$—$NH_2$. Other preferred compounds are those in which $R_2$ is $(CH_2)2$, $X_1$ is O and $R_3$ is H.

In another preferred aspect of the above embodiment, $R_2$ is $(CH_2)_3$, $X_1$ is NH and $R_3$ is H. Further preferred compounds are those in which $R_2$ is $(CH_2)_4$, $X_1$ is NH and $R_3$ is H. In additional preferred compounds, $R_2$ is $(CH_2)_5$, $X_1$ is NH and $R_3$ is H.

In a further group of preferred compounds, $R_2$ is $(CH_2)_6$, $X_1$ is NH and $R_3$ is H. Yet another group of preferred compounds are those in which $R_2$ is $(CH_2)_3$, $X_1$ is NH and R3 is CO—CH2—$NH_2$.

In additional preferred compounds, $R_2$ is $(CH_2)_3$, $X_1$ is NH and R3 is CO—NH—$CH_3$. In another group of preferred compounds, $R_2$ is CO—CH($NH_2$), $X_1$ is absent and $R_3$=—$CH_2$—$CH_2$—$NH_2$.

The present invention also relates to piperazine based cytofectin of the following structure:

wherein $R_1, R_2, R_4$ and $R_5$ are independently H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups each of which may contain 0–5 heteroatoms;

$R_3$ and $R_6$ are independently absent, H, $R_1$ as defined above, or an amino acid, peptide, polypeptide, protein, nucleic acid, nucleotide or nucleoside, polynucleotide, polynucleoside, mono-, di- or polysacchararide, or other bioactive or pharmaceutical agent or the following structure:

wherein $R_7$ through $R_{12}$ are independently absent, H, linear, branched, unsubstituted or substituted $C_1$–$C_{23}$ alkyl, acyl, alkene, or heteroalkyl groups having from 0 to 6 sites of unsaturation and containing from 0 to 5 heteroatoms, or cyclic or aryl groups or independently comprise an amino acid, nucleotide, polynucleotide, mono-, di- or polysaccharide, or other bioactive or pharmaceutical agent chemically linked thereto;

G is absent, O, N, NH, S, SH, Se, C, CH, or $CR_1$;
T is O, N, S, Se, or C;
A is O, N, S, Se, or C;
$Y_1$ and $Y_2$ are independently absent, O, N, NH, S, or Se;
$X_1$ and $X_2$ are independently absent, O, N, NH, S, or Se;
m and p are independently 0–6;
W is a pharmaceutically acceptable anion; and
wherein $R_2$—$X_1$—$R_3$ and $R_5$—$X_2$—$R_6$ are not simultaneously a lower alkyl of up to 6 carbons inclusive.

In a preferred aspect of the above embodiment, m and p are 2. Preferentially, in this preferred aspect $Y_1$ and $Y_2$ are O. Additional preferred compounds are those in which $R_5$ and $R_2$ are selected from the group consisting of absent, $CH_2$, $(CH_2)_2$, $(CH_2)_3$, $(CH_2)_4$, $(CH_2)_5$ and $(CH_2)_6$. More preferentially, $R_1$ and $R_4$ are selected from the group consisting of $C_{10}H_{21}$, $C_{12}H_{25}$, and $C_{14}H_{29}$. In highly preferred compounds, $X_1$ and $X_2$ are selected from the group consisting of absent, NH and O.

In one group of preferred compounds, $R_1$ and $R_4$ are $C_{12}H_{25}$, $R_2$ is $CH_3$; $X_1$ and $R_3$ are absent, $R_5$ is $CH_2CH_2CH_2$, $X_2$ is NH and $R_6$ is H.

Another aspect of the present invention relates to a method of delivering a molecule into a cell comprising the steps of (a) contacting the molecule with an effective amount of any of the cationic lipids having the formulas drawn above to form a complex with the lipid; and (b) contacting a cell with the lipid complex formed in step (a);

whereby a biologically effective amount of the molecule is inserted into the cell.

In a preferred version of the above method, the molecule is an anionic molecule.

In another aspect of the above method, the complex additionally includes one or more additional lipids. Preferentially, the additional lipids are selected from the group consisting of neutral lipids, phospholipids, and cholesterol.

In one aspect of the method, the cells are in vitro. In another aspect of the invention, the cells are in vivo. Preferentially, the cells are in an assay selected from the group consisting of the murine lung transfection, murine intraperitoneal tumor, murine intramuscular, porcine or rabbit intraarterial, Renca tumor, or subcutaneous tumor assays.

In a preferred embodiment of the method, the anionic molecule is mRNA. In another preferred embodiment of the method, the anionic molecule is DNA.

DETAILED DESCRIPTION OF THE PREFERRED EMBODIMENT

It has been discovered that quaternary nitrogen compounds are effective cytofectins that have advantageous characteristics resulting from their specific structures. The present invention relates to piperazine based cytofectins in which at least one of the ring nitrogens is quatranized. In addition to lipophilic moieties, the cytofectins of the present invention have a hydrocarbon chain which includes at least one heteroatom linked to at least one of the ring nitrogens.

The inclusion of a heteroatom in the hydrocarbon chain provides several benefits. For example, the present compounds can be derivatized to form transfection agents having the ability to interact more specifically with the cell membrane and to achieve higher levels of transfection. The present compounds can be adapted to target key receptors and enzymes on cellular surfaces and are thus suitable for use in the discovery and exploitation of important factors in molecular recognition.

The present cationic lipids can also be attached to substances that are delivered intracellularly for achieving a particular biological purpose. A functional group such as carbamyl, carboxyl, ureyl, thiol, ester, ether, thioureyl, phosphoryl, or guanidyl groups is used to attach a cell targeting moiety or a therapeutic molecule to the cytofectin. Various types of targeting moieties and therapeutic moieties are discussed below.

Additionally or alternatively, the functional group can be used as a linker to attach groups that can increase the polar charge density of the cytofectin, thus enhancing transfection efficiency.

Bioactive Headgroups on the Cytofectins (a) Targeting Species

A cytofectin according to the present invention can include a molecular species having a biological cell targeting activity as a terminal group. Within this class are cytofectins comprising cell receptor-specific molecules. Typically, the receptor-specific peptides or amino acids are linked as amides. Examples of preferred peptides which could be joined to the cytofectins of the present invention include the chemotactic peptides methionine-leucine-phenylalanine (Met-Leu-Phe), and pGlu-Pro-His. Other ligands for cell surface receptors that can be attached to cytofectins of the invention comprise peptidomimetic analogs; many viral attachment and internalization peptides, lactose and other di- and polysaccharides; acetylcholine analogs; and folic acid derivatives.

(b) Therapeutic Agents

A cytofectin according to the invention can include as a terminal group a bioactive molecular species. An example of a preferred bioactive species which could be linked to the compounds of the present invention is the thyrotropin-releasing hormone pGlutamate-histidine-proline.

(c) Cellular and Intracellular Targeting

A cytofectin according to the invention can comprise a terminal group bearing a ligand that can specifically bind to a cell membrane or intracellular target to effect a desired physiological response. Appropriate ligands may comprise peptides that are viral epitopes, hormones, enzyme substrates, monosaccharides, disaccharides, oligosaccharides, carbohydrates, cofactors, drugs, lectins, oligonucleotides, and nucleic acids. Preferred species among this group are cytofectins comprising chloroquine and other lysosomotropic agents, nuclear localization peptides, corticosteroids and viral peptides or proteins.

(d) Groups Influencing Transfection Efficiency

The cytofectins of the present invention may be linked to groups which influence their transfection efficiencies. Such groups may be amino acids, peptides, polypeptides, proteins, nucleic acids, nucleotides, polynucleotides, mono, di- or polysaccharides. Both traditional and non-traditional linkages for appending these building blocks to the cytofectins are contemplated. Additionally, the amino acids, peptides, polypeptides, or proteins may include unusual or modified amino acids not generally found in living organisms. Such unusual or modified amino acids include but are not limited to the modified and unusual amino acids listed in 37 C.F.R. § 1.822. In addition, such amino acids may be synthetic amino acids not found in nature. It is intended that the claims to the cytofectins in this patent encompass compounds in which any moiety is linked to a piperazine backbone through a heteroatomic hydrocarbon chain. Thus, the claims are not avoided by combining or linking the cytofectin with another moiety.

Additionally, the heteroatomic group alone may beneficially influence transfection efficiency. As discussed above with regard to BAE-DMRIE, the identity of the heteroatomic group may have significant effects on transfection efficiency.

(e) Formulations

The compounds of the present invention can be used in formulations to transfect mammalian cells both in vitro and in vivo. Formulations for transfection are known to those skilled in the art and are disclosed, together with methods for their preparation, for example, in U.S. Pat. No. 5,264,618 to Felgner, U.S. Pat. No. 5,334,761 to Gebeyehu et al, and Felgner et al. (*J. Biol. Chem.* 269:2550–2561, 1994), which are hereby incorporated by reference. The cationic lipids of the invention can be combined with amphipathic lipids such as phospholipids and with neutral lipids, such as cholesterol to form lipid vesicles, which can be liposomes, unilammelar vesicles, micelles, or simple films.

(f) Use of Claimed Compounds for Gene Therapy, Vaccination and Transfection

Cationic liposomes are known to be useful for facilitating entry of polynucleotides, macromolecules, and small molecules into cells of the blood vessels, the systemic circulation, lung epithelial cells, brain tissue and frog embryos (Xenopus).

The cationic lipids of the present invention are particularly useful in facilitating gene therapy. The use of the disclosed cationic lipids to facilitate delivery of mRNA or DNA to living organisms, such as vertebrates, including birds, mammals, fish, and amphibians is particularly contemplated. Specifically, delivery to humans and domestic animals is contemplated. The use of cationic lipids for this purpose, as well as transfection protocols, is reported by Nabel et al. (*Human Gene Therapy* 3:399–410, 1992), U.S. Pat. No. 5,459,127 to Felgner, and Wheeler et. al, 1280 *Biochem. Biophys. Acta:* 1–11 (1996).

The polynucleotides delivered by the cytofectins of the present invention preferably encode an immunogenic or therapeutic peptide or polypeptide. This method can thus be used for polynucleotide vaccinations as well as gene therapy. Where the cationic lipids of the present invention are used to introduce DNA into a host organism, the DNA may contain sequences in addition to the coding region, e.g., suitable promoters such as the CMV, RSV or SV40 promoters, ribosome binding sites, and polyadenylation sites.

It is also noted that the cytofectins of the present invention are useful in transfecting cells in vitro. Although various compounds within the scope of the present invention are somewhat tissue specific in vivo, most or all are useful for transfection of cultured cells in vitro. For any particular candidate cytofectin of the present invention, its relative transfection efficacy in vitro and in various tissues in vivo can be readily ascertained using screening assays such as those disclosed in Examples 2–11 or other standard transfection assays. With this information, one of skill in the art can readily practice the invention using art-recognized formulations and dosages.

(h) Representative Piperazine Based Cytofectins and their Nomenclature

Table I below lists representative piperazine based cytofectins used in the following Examples, along with their acronyms. The singly quatranized compounds listed in Table I have the structure shown below in which m and p are both 2 and Y1 and Y2 are both O.

The doubly quatranized compounds listed in Table I have the structure shown below in which m and p are both 2 and Y1 and Y2 are both 0.

The system of nomenclature presented in Table I is used consistently throughout the present application. The designation BP refers to the bis-piperazine backbone. The acronyms MOE, LOE, and DOE refer to the lipophilic moieties MyristylOxyEthyl ($C_{14}H_{29}O(CH_2)_2$), LaurylOxyEthyl ($C_{12}H_{25}(CH_2)_2$), and DecylOxyEthyl respectively. Other acronyms relate to the hydrocarbon chain having at least one heteroatom as follows:

HE=hydroxyethyl; GA=gamma amino; DA=delta amino; FA=funf amino; HA=hexyl amino; Me=methyl; Gly-G= glycine amide; DAB=2,4-diaminobutyric acid amide; DiMe=dimethyl; and GMU=gamma methyl urea.

The present invention is described below in detail using the following examples, but the methods disclosed are applicable for the preparation of all cationic lipids covered by the scope of the invention and are not limited to the examples. All of the temperatures indicated in the Examples are in degrees Celsius and are uncorrected.

EXAMPLE 1

Synthesis of Bis-Piperazine Cytofectins

The chemical reactions described below are disclosed in terms of their general application to the preparation of the cationic lipids of the invention. Occasionally, the reaction may not be applicable as described to each molecular species within the disclosed scope. The compounds for which this occurs will be readily recognized by those skilled in the art. In all such cases, either the reactions can be successfully performed by conventional modifications known to those skilled in the art, that is, by changing to alternative conventional reagents, or by routine modification of reaction conditions. Alternatively, other reactions disclosed herein, in the references cited herein relating to the synthesis of other classes of cytofectins such as the DOTMA compounds of Felgner et al. *J. Biol. Chem.* 84:7413–7417, 1987, or in the conventional chemical literature will be applicable to the preparation of the compounds of the invention. In all preparative methods, all starting materials are known or readily preparable from known starting materials.

A. Synthesis of a Representative Singly Quatranized Compound (GA-LOE-BP)

The following example is provided as a representative synthesis of singly quatranized piperazine based cytofectin.

TABLE I

Singly Quatranized Compounds
C-14 Alkyl Chains $R_1$ and $R_4$ = $C_{14}H_{29}$

| | |
|---|---|
| HE-MOE-BP | $R_2 = CH_2CH_2$ ; $X_1 = O$; $R_3 = H$ |
| GA-MOE-BP | $R_2 = CH_2CH_2CH_2$; $X_1 = NH$; $R_3 = H$ |
| DAB-G-MOB-BP | $R_2 = CO-CH(NH_2)$; $X_1 = $ absent; $R_3 = -CH_2-CH_2-NH_2$ |

C-12 Alkyl Chains $R_1$ and $R_4$ = $C_{12}H_{25}$

| | |
|---|---|
| Me-LOE-BP | $R_2 = CH_3$; $X_1 = $ absent; $R_3 = $ absent |
| HE-LOE-BP | $R_2 = CH_2CH_2$; $X_1 = O$; $R_3 = H$ |
| GA-LOE-BP | $R_2 = CH_2CH_2CH_2$; $X_1 = NH$; $R_3 = H$ |
| DA-LOE-BP | $R_2 = CH_2CH_2CH_2CH_2$; $X_1 = NH$; $R_3 = H$ |
| FA-LOE-BP | $R_2 = CH_2CH_2CH_2CH_2CH_2$; $X_1 = NH$; $R_3 = H$ |
| HA-LOE-BP | $R_2 = CH_2CH_2CH_2CH_2CH_2CH_2$; $X_1 = NH$; $R_3 = H$ |
| Gly-G-LOE-BP | $R_2 = CH_2CH_2CH_2$; $X_1 = NH$; $R_3 = CO-CH_2NH_2$ |
| GMU-LOE-BP | $R_2 = CH_2CH_2CH_2$; $X_1 = NH$; $R_3 = CO-NH-CH_3$ |

C-10 Alkyl Chains $R_1$ and $R_4$ = $C_{10}H_{21}$

| | |
|---|---|
| HE-DOE-BP | $R_2 = CH_2CH_2$; $X_1 = O$; $R_3 = H$ |
| GA-DOE-BP | $R_2 = CH_2CH_2CH_2$; $X_1 = NH$; $R_3 = H$ |
| DA-DOE-BP | $R_2 = CH_2CH_2CH_2CH_2$; $X_1 = NH$; $R_3 = H$ |

Doubly Quatranized Compounds $R_1$ and $R_4$ = $C_{12}H_{25}$

| | |
|---|---|
| DiMe-LOB-BP | $R_2$ and $R_5 = CH_3$; $X_1$, $X_2$, $R_3$, and $R_6 = $ absent |
| Me,GA-LOE-BP | $R_2 = CH_3$; $X_1$ and $R_3 = $ absent; $R_5 = CH_2CH_2CH_2$; $X_2 = NH$; $R_6 = H$ |

Those skilled in the art will appreciate that the compounds listed in Table I are representative of the compounds of the present invention and that the present invention is not limited to the compounds in Table I. Additionally, those skilled in the art will appreciate that doubly quatranized piperazine cytofectins having various combinations of the substituents listed in Table I with regard to the singly quatranized compounds are specifically contemplated by the present invention.

Those skilled in the art will appreciate that synthesis of piperazine based cytofectins having groups other than lauryl linked to the piperazine backbone can be readily accomplished by merely substituting the desired alkylmethanesulfonate, for example myristylmethane sulfonate or decylmethane sulfonate, for the dodecylmethane sulfonate of the following synthesis. Similarly, one desiring to synthesize a piperazine based cytofectin in which the lipophilic chain is linked to the piperazine backbone via an amine bond could simply substitute bis-aminoethyl-piperazine for bis-hydroxyethylpiperazine in the synthesis below.

N,N¹-bis-(2-dodecyloxyethyl)-piperazine [LOE-BP]

A dry flask equipped with magnetic stirring was maintained under an argon atmosphere then charged with sodium hydride (60% in oil, 1.47 gr, 37 mmol). After trituration with dry hexane (4⊗15 mL) anhydrous tetrahydrofuran (120 mL) was added and stirring was initiated to afford a thin slurry. Bis-hydroxyethyl-piperazine (2.79 gr, 16 mmol) was added all at once as a solid, after which the reaction was brought to reflux and maintained at that temperature overnight. To the refluxing slurry a solution of dodecylmethane sulfonate (10.2 gr, 38 mmol) in anhydrous tetrahydrofuran (25 mL) was added and the reaction kept at reflux for a further three days. The reaction was cooled and the slurry was vacuum filtered through a 1 cm plug of Celite with reaction vessel and filtration apparatus being rinsed with tetrahydrofuran (100 mL). The filtrates were combined then evaporated and the residue partitioned between ethyl ether (230 mL) and 0.2 N sodium hydroxide (50 mL). The phases were separated and the organic layer was washed twice with water (50 mL) then dried over anhydrous magnesium sulfate. The solution was filtered through filter paper, and the filtrate evaporated to afford the crude product. Column chromatography on silica gel using step gradient elution of 1:9 ether:hexane to neat ether afforded TLC homogenous material (3.6 gr, 44%). $^1$H-NMR (300 mHz, CDCl$_3$, TMS); δ=3.54 (t, J-6 Hz, 4H), 3.41 (t, J=6.6 Hz, 4H), 2.2.6–2.55 (overlapping m, 12H), 1.55 (m, 4H), 1.26 (s, 36H), 0.88 (t, J=6.6 Hz, 6H). IR (KBr pellet): CM$^{-1}$ 2900, 2840, 1460, 1295, 1320, 1115, 715.

(±)-N-(3-phthalimido)propyl-N,N'-(bis-2-dodecyloxyethyl)-piperazinium Bromide [γ-Phth-LOE-BP]

In a dry flask LOE-BP (2.16 gr, 4.2 mmol), anhydrous dimethylformamide (10 mL) and N-(3-bromopropyl) phthalimide (1.42 gr, 5.3 mmol) were combined in the order given while maintaining an argon atmosphere. The flask was tightly stoppered then immersed in a pre-equilibrated oil bath at 105° C. and magnetic stirring was initiated. The solution became homogenous within 2 minutes. After stirring for 3 days at the indicated temperature the reaction was cooled and the solvent was removed by vacuum distillation. Chromatography of the residue on silica gel (90:10:0.25:0.25 chloroform:methanol:ammonium hydroxide:water, isocratic elution) afforded TLC homogenous material (1.70 gr, 52%%). $^1$H-NMR (300 mHz, CDCl$_3$, TMS): δ7.86 (m, 2H), 7.75 (m, 2H), 4.16 (m, 2H), 3.95 (m, 2H), 3.87–3.82 (overlapping m, 4H), 3.72 (m, 2H), 3.54–3.45 (overlapping m, 4H), 3.39 (t, J=6.6 Hz, 4H), 2.97 (m, 2H), 2.90 (m, 2H), 2.70 (t, J=5 Hz, 2H), 2.31 (m, 2H), 1.54–1.45 (m, 4H), 1.25 (s, 36H), 0.88 (t, J=6.6 Hz, 6H). IR (melt, film on NaCl): cm$^{-1}$ 2900, 2850, 1770, 1700, 1460, 1390, 1365, 1110, 715.

(±-N-(3-aminopropyl)-N,N'-bis-(dodecyloxyethyl)-piperazinium Bromide ("GA-LOE-BP")

A solution of γ-PHth-LOE-BP (1.77 gr, 2.27 mmol) in absolute ethanol (33 mL) was prepared by stirring at ambient temperature. To the clear mixture anhydrous hydrazine (1.6 mL, 51 mmol) wa added in a steady stream. The flask was then flushed with argon, tightly stoppered and stirred at ambient temperature overnight. After this period the thick slurry was diluted with chloroform (65 mL) and stirred for about 30 minutes, then vacuum filtered through a medium glass frit. The reaction vessel and filtration apparatus were rinsed with an additional 65 mL of chloroform in two portions. The combined filtrates were evaporated in vacuo at less than 40° C. to a small volume. The residue was then partitioned between chloroform (350 mL) and 0.1 N sodium hydroxide (150 mL). The aqueous phase was washed two more times with chloroform (150 then 125 mL), and the combined organic phases were dried over anhydrous sodium sulfate overnight. The clear solution was then filtered through filter paper and evaporated. The residue was treated with high vacuum overnight then dissolved in chloroform (10 mL) and filtered through a 0.2 μ PTFE filter. The filtrate was evaporated and the residue then treated with high vacuum overnight to afford 1.37 gr (93%) of TLC homogenous product. (amine coated silica gel, 85:15:0.25:0.25 chloroform:methanol:ammonium hydroxide:water, R$_f$=0.51). $^1$H-NMR (300 mHz, CDCl$_3$, TMS): δ4.01 (m, 2H), 3.93–3.74 (overlapping m, 6H) 3.62–3.50 (overlapping m, 4H), 3.46 (t, J=6.6 Hz), 3.40 (t, J=6.7 Hz, 2H), 2.94 (t, J=4.7 Hz, 4H), 2.88 (t, J=6.1 Hz, 2H), 2.71 (t, J=5.1 Hz, 2H), 2.0 (m, 2H), 1.55 (m, 4H), 1.26 (s, 36H), 0.88 (t, J=6.3 Hz, 6H). IR (melt on Nacl): cm$^{-1}$ 3400 (br), 3300 (s), 1520, 1360, 1110, 715.

Figure 1:
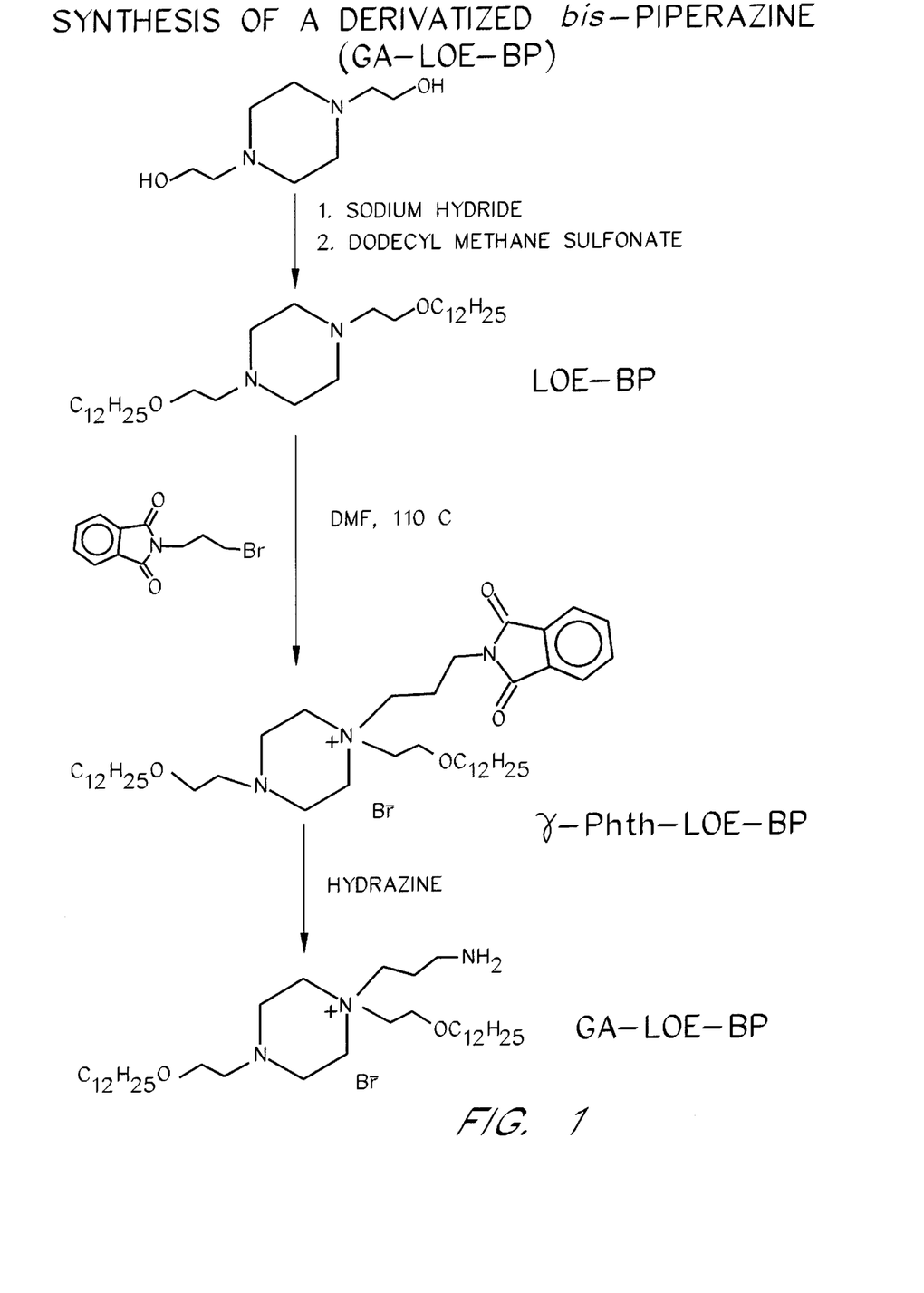
FIG. 1 shows the synthesis of GA-LOE-BP.

The synthetic scheme for GA-LOE-BP is shown in FIG. 1.

B. Synthesis of a Representative Doubly Quatranized Compound (Me,GA-LOE-BP)

N,N¹-bis-(2-dodecyloxyethyl)-piperazine [LOE-BP] and (±)-N-(3-phthalimido)propyl-N,N'-(bis-2-dodecyloxyethyl)-piperazinium bromide[γ-Phth-LOE-BP] were synthesized as described above.

(+)-N-methyl-N'(3-phthalimido)prop yl-N,N'-(bis-2-dodecyloxyethyl)-piperazinium Bromide [Me,γ-Phth-LOE-BP]

In a dry flask γ-Phth-LOE-BP (0.44 gr, 0.56 mmol) dimethylformamide (1.3 mL) and methyl iodide (0.15 mL, 0.342 gr, 3 mmol) were combined. The flask was tightly stoppered then immersed in a pre-equilibrated oil bath at 105° C. and magnetic stirring was initiated. After stirring for 3 days at the indicated temperature the reaction was cooled and the solvent was removed by vacuum distillation. Chromatography of the residue on silica gel (90:10:0.25:0.25 to 85:15:0.25:0.25 chloroform:methanol:ammonium hydroxide:water; step gradient) afforded TLC homogenous material (0.336 gr, 67%), (silica gel, 80:20:0.25:0.25 chloroform:methanol:ammonium hydroxide:water, R$_f$=0.28). $^1$H-NMR (300 mHz, CDCl$_3$, TMS): δ7.84 (m, 2H), 7.73 (m, 2H, 4.7–4.3 (overlapping m, 14H), 3.9 (overlapping m, 9H), 3.5–3.4 (overlapping m, 4H), 2.34 (m, 2H), 1.54–1.45 (m, 4H), 1.25 (s, 36H), 0.88 (t, J=6.2 Hz, 6H). IR (KBr):cm$^{-1}$ 2920, 2850, 1770, 1710, 1460, 1390, 1360, 1120, 715.

(+)-N-(3-aminopropyl)-N'-methyl-N,N'-(bis-2-dodecyloxyethyl)-piperazinium Bromide [GA,Me-LOE-BP]

A solution of Me,γ-Phth-LOE-BP (0.32 gr, 0.49 mmol) in absolute ethanol (10 mL) and chloroform (5 mL) was prepared by stirring at ambient temperature. To the clear solution anhydrous hydrazine (0.3 mL, 9.6 mmol) was added in a steady stream. The flask was then flushed with argon, tightly stoppered and stirred at ambient temperature overnight. After this period the thick slurry was diluted with chloroform (30 mL) and stirred for about 30 minutes, then vacuum filtered through a medium glass frit. The reaction vessel and filtration apparatus were rinsed with an additional 60 mL of chloroform in two portions. The combined filtrates were evaporated in vacuo at less than 40° C. to a small volume. Chloroform (100 mL) was added and then removed in vacuo and the residue subjected to high vacuum for 4 days. The white solid was then dissolved in 9:1 chloroform:ethanol (20 mL) and filtered through a 0.2 $\mu$ PTFE filter. The filtrate was evaporated and the residue then treated with high vacuum overnight to afford a brittle white solid. This residue was dissolved in chloroform:methanol (110 mL, 8:3 ratio) and washed with 0.2 N sodium hydroxide (30 mL). The aqueous phase was washed with chloroform (15 mL), and the combined organic phases were dried over anhydrous sodium sulfate. The clear solution was then filtered through filter paper and evaporated. The residue was treated with high vacuum overnight then dissolved in neat chloroform (10 mL) and filtered through a 0.2 $\mu$ PTFE filter. The filtrate was evaporated and the residue then treated with high vacuum overnight to afford the product (0.23 gr, 59%). $^1$H-NMR (300 mHz, CDCl$_3$, TMS): $\delta$4.7–4.3 (overlapping m, 14H), 3.9 (overlapping m, 5H), 3.6–3.3 (overlapping m, 6H), 2.7–2.4 (overlapping m, 6H), 1.54–1.45 (m, 4H), 1.25 (s, 36H), 0.88 (t, J=6.2 Hz, 6H). IR (melt on NaCl): cm$^{-1}$ 3400 (br), 2910, 2840, 1630, 1455, 1365, 1110, 715.

Figure 2:
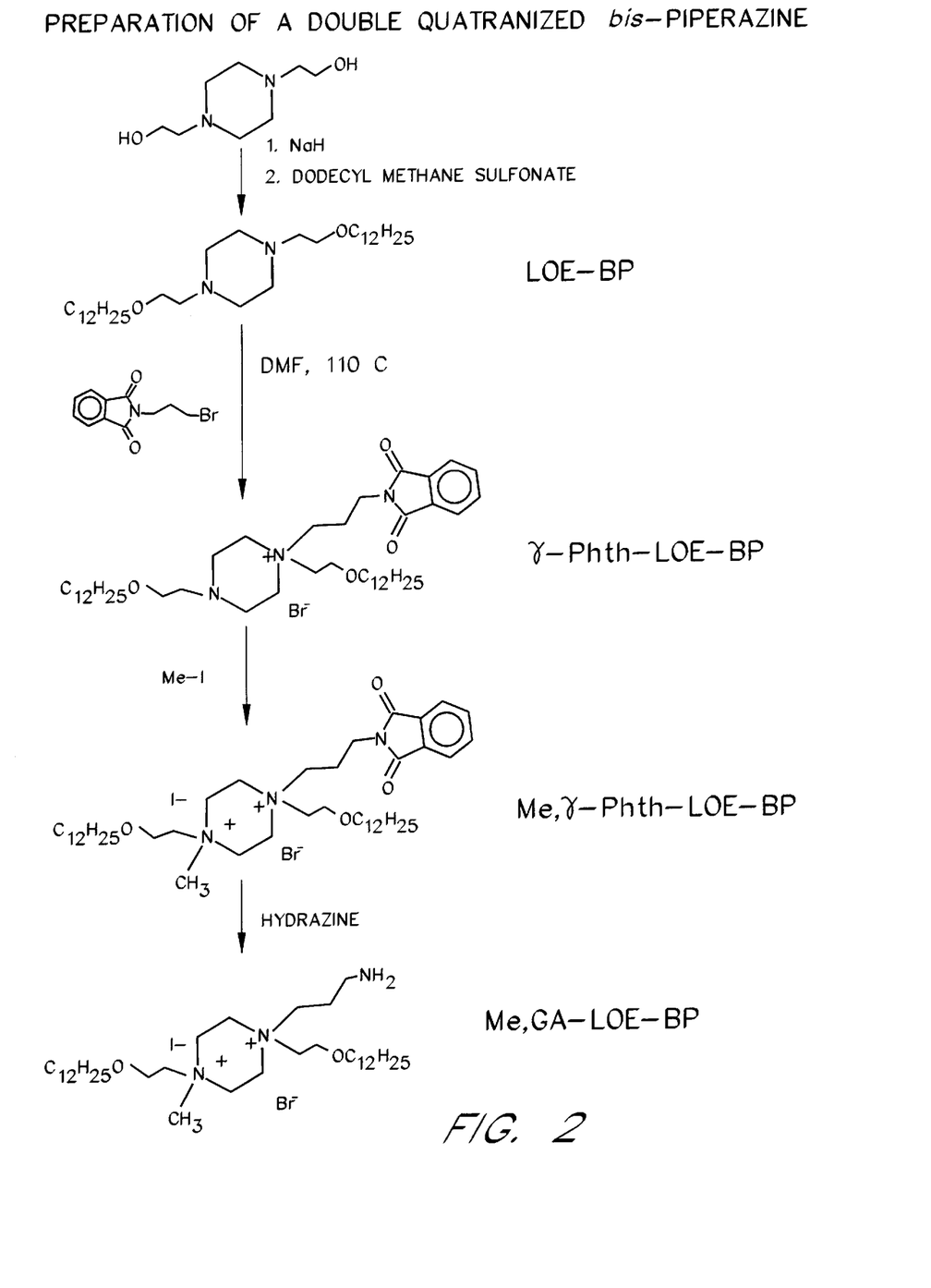
FIG. 2 shows the synthesis of Me, GA-LOE-BP.
Figure 3A:
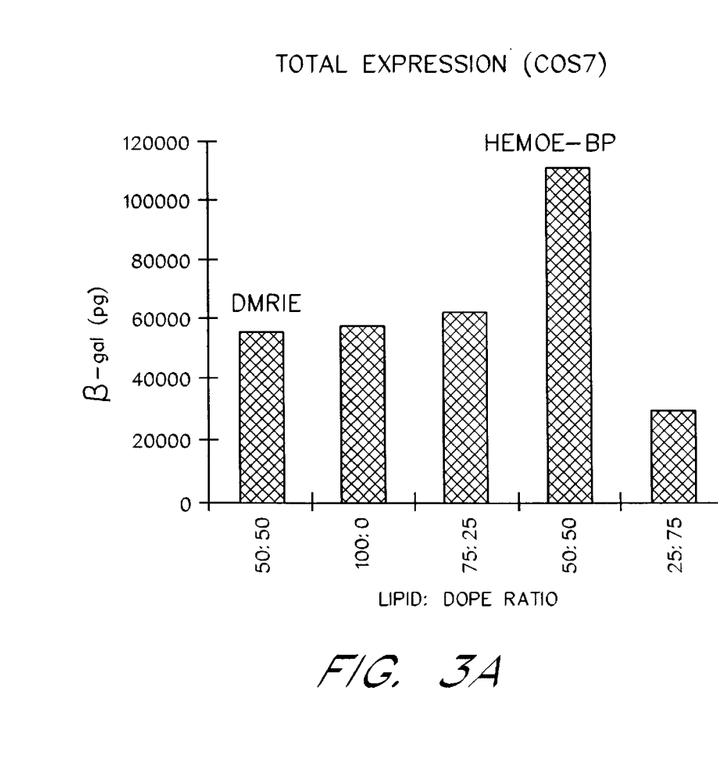
FIGS. 3A–3D compare the transfection efficiencies of DMRIE and HE-MOE-BP in both COS7 and C2C12 cells.
Figure 3B:
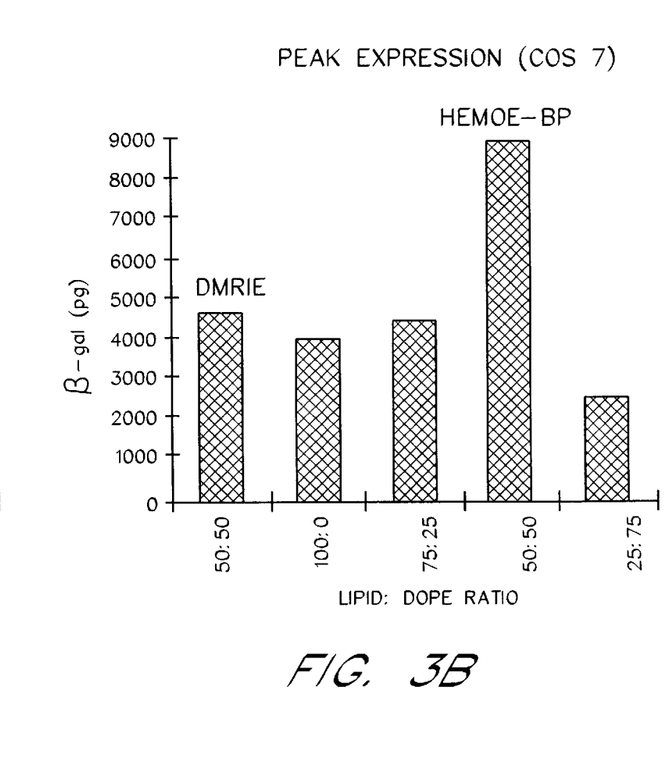
Figure 3C:
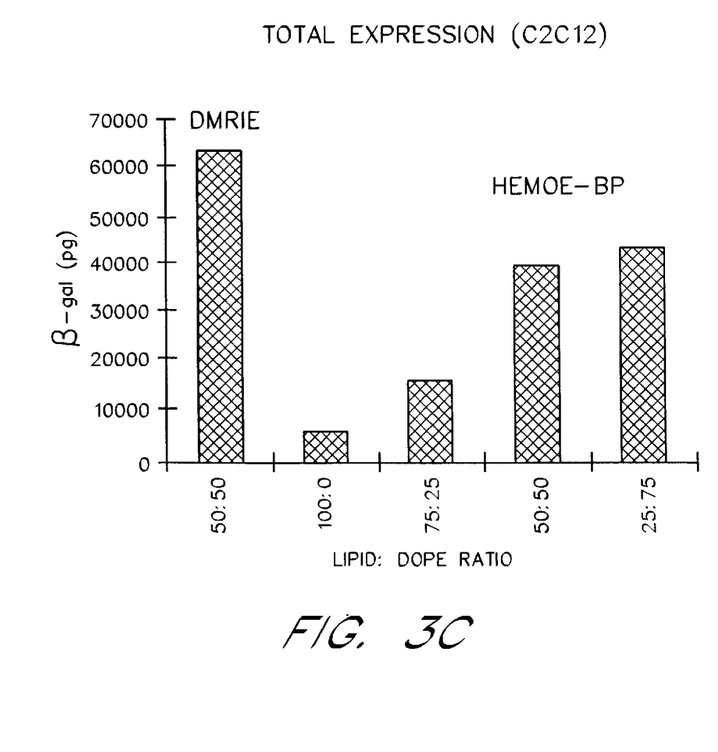
Figure 3D:
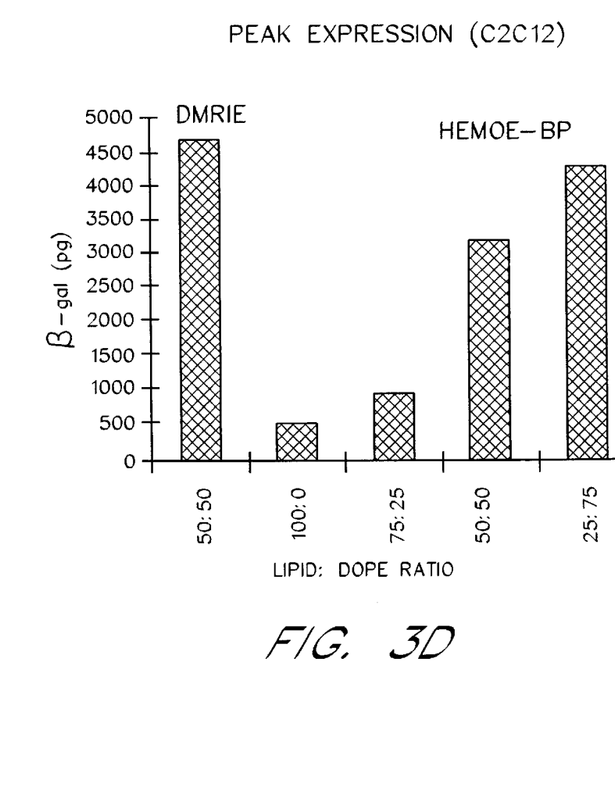

FIG. 2 shows the reaction scheme for the synthesis of a representative double quatranized piperazine based cytofectin, Me$_2$GA-LOE-BP.

Those skilled in the art will appreciate that the methods described above may be used to prepare a variety of double quatranized piperazine based cytofectins. The non-lipophilic moieties attached to each of the quatranized nitrogens may be identical or different. In one embodiment of the present doubly quatranized cytofectins, both of the non-lipophilic moieties attached to the quaternary nitrogens are heteroatomic. In an alternative embodiment, only one of the non-lipophilic moieties is heteroatomic.

Of course, those skilled in the art are aware that in the case of molecules having more than one reactive functional group, it is necessary to block or mask one or more of those groups which are not intended to participate in the particular coupling reaction. Synthesis in conjunction with screening can be used to efficiently select the most effective cytofectin for a defined application.

EXAMPLE 2

Effect of Formulation on in vitro Transfection: Comparison of HE-MOE-BP with DMRIE Cytofectin Solutions of a selected cytofectin in chloroform were prepared on a weight to volume (w/v) basis. Aliquots of cationic lipid and neutral lipid (when used) were transferred aseptically to sterile vials in amounts calculated to provide the relative and absolute lipid concentrations desired upon reconstitution with 1 ml of aqueous vehicle. Bulk chloroform was removed with a stream of dry nitrogen, and the vials were treated with high vacuum overnight to remove any residual solvent.

DNA-lipid Complexes

Plasmid DNA at 5 mg/ml of phosphate buffered saline (PBS) as well as the dried, formulated cytofectin-neutral lipid mixture were suspended in OPTIMEM™ (Gibco BRL) and mixed together in 96 well plates at the desired mass/ molar ratio as indicated. The DNA-lipid complexes were added to the cells within 2 hours after mixing.

Transfection

Cell Lines

The cell lines used were obtained from the American Type Culture Collection (ATCC, Rockville, Md.) as follows: COS7 monkey kidney cells (ATCC CRL 1651); and C2C$_{12}$ mouse myoblast muscle cells (ATCC CRL 1772).

All cells were passaged 1:5 to 1:10 in 10% fetal bovine serum (FBS) and Dulbecco's Modified Eagles medium (DMEM). All cells were expanded through 10 doubling passages upon receipt and aliquots were stored frozen. Upon re-expansion, all cells were used for transfection studies before another 10 passages.

Transfection Assays

On day 0, 20,000 cells in 100 microliters 10% FEBS/ 90%DMEM were seeded into each well of 96-well culture plates (Nunc) and cultured overnight in a 5% CO$_2$ incubator at 37° C. On Day 1, the medium was aspirated carefully without dislodging cells, and 100 microliters of HE-MOE-BP/pRSV lacZ/DOPE in serum-free OPTIMEM™ (A modification of MEM (Eagles) which contains HEPES buffer, 2,400 mg/L sodium bicarbonate, hypoxanthine, thymidine, sodium pyruvate, L-glutamine, trace elements, growth factors, and phenol red reduced to 1.6 mg/L, but no calcium chloride) (Gibco BRL) was added. DMRIE was used as a reference standard. The lacZ gene encodes the enzyme $\beta$-galactosidase which can be assayed colorimetricaly. The cationic lipid:DOPE ratios varied for each well. After 4 hours of culture, 50 microliters 30% FBS/70% OPTI-MEM™ (A modification of MEM (Eagles) which contains HEPES buffer, 2,400 mg/L sodium bicarbonate, hypoxanthine, thymidine, sodium pyruvate, L-glutamine, trace elements, growth factors, and phenol red reduced to 1.6 mg/L, but no calcium chloride) was added to each well. On Day 2, each well received 100 microliters 10%FEBS/90% OPTIMEM™. On Day 3, the medium was removed and 50 microliters lysis buffer (0.1% Triton-X$_1$00 in 250 mM Tris, pH 8.0) was added and the plates were stored at 70° C. for at least 20 hours. After thawing, the well media were assayed for their content of $\beta$-galactosidase enzyme activity according to Felgner et al. (J. Biol. Chem. 269:2550–2561, 1994).

The results (FIGS. 3A–3D) show that both total expression and peak expression of $\beta$-gal in COS7 cells were optimal at a HE-MOE-BP:DOPE ratio of 50:50 and in C2C$_{12}$ cells at a HE-MOE-BP:DOPE ration of 25:75. HE-MOE-BP compared favorably with DMRIE in these in vitro assays. These experiments indicate that the present piperazine based cytofectins promote efficient transfer of DNA across the cell membrane in vitro followed by functional expression of the gene within the cell. The screening assay used in these tests is useful for demonstrating transfection activity and for optimizing the cytofectin/colipid ratio.

EXAMPLE 3

Analysis of Piperazine Based Cytofectins in the Intralung and Intraperitoneal Transfection Assays A. Intralung Transfection Assay Adult (4–16 weeks) female BALB/c mice were lightly anesthetized with metophane and 132 $\mu$g chloramphenicol acetyltransferase (CAT DNA±cationic lipid in 100 $\mu$l USP saline or water was delivered intranasally using a disposable sterile, plastic insulin syringe fitted with a small plastic catheter. Cationic lipids were mixed with 1 molar equivalent of DOPE in chloroform, and the solvent was evaporated and then the residue was treated with high vacuum to afford a lipid film. Cationic liposomes were prepared by adding water to this film and vortexing for about 1 minute. Appropriate volumes of plasmid DNA in water and cationic liposomes in water were combined at ambient temperature and vortexed for about 30 seconds to afford complexes at a 2:1 (mol:mol) nucleotide:cytofectin ratio. All fluids and syringes were equilibrated to room temperature and the delivery of the single 100 µl volume of DNA required less than one minute. Two or three days post-delivery, the mice were killed by sodium pentobarbital overdose, and the lungs extracted as follows.

Lungs were immediately frozen and stored at −78° C. Frozen lungs were individually pulverized into a fine powder by grinding over 0.4 ml frozen lysis buffer in a 1.5 ml tube using a reversible drill and a bit that just fits into the tube, and the powder is stored in the same tube at −78° C. until extraction. Frozen powders are thawed and 100 µl Reporter Lysis Buffer from Promega (Catalog #E397A) was added to each. The samples were vortexed for 15 minutes, frozen-thawed three times using alternating liquid nitrogen and room temperature water baths and centrifuged three minutes at 10,000×g. The supernatant was transferred to another 1.5 ml tube and the extraction process repeated (without freeze-thawing) after adding another 500 µl lysis buffer to the pellet. The second supernatant was combined with the first and stored at −78° C.

The cationic piperazine based lipids used were HE-MOE-BP, GA-MOE-BP, GA-LOE-BP, and BA-LOE-BP. GAP DLRIE was included for comparison.

CAT assays were performed by the radioactive partition method of Sankaran (*Anal. Biochem.*, 200:180–186, 1992) or by using a CAT ELISA kit (Boehringer Mannheim, Indianapolis, Ind.). Briefly, CAT tissue homogenates were disrupted by freeze-thawing three times in an ethanol/dry ice bath. Cellular debris was removed by centrifugation and the protein extract was incubated with $^{14}$C-chloramphenicol and acetyl CoA. The chloramphenicol was extracted with ethyl acetate and thin layer chromatography was performed to determine the percent of $^{14}$C-chloramphenicol converted by the extracted cellular protein. Cell extracts were standardized to 2 µg protein incubated for 20 minutes. Tissue extracts were standardized to 200 µg protein incubated for four hours.

Standard curves were constructed using purified enzyme (Sigma, St. Louis, Mo.) spiked into lung extracts or enzyme provided in the ELISA kit. The two CAT assay methods yielded equivalent pg CAT per sample from the same set of extracts.

B. Intraperitoneal Transfection Assay

The transfection efficiencies of the piperazine based cytofectins tested in the intralung assay above were also evaluated in the murine intraperitoneal model. Two hundred thousand murine B16 tumor cells in 500 µl RPMI were injected intraperitoneally into C57/B16 mice at day 0. At day 7–14 mice were injected intraperitoneally with a DNA/cytofectin/saline solution. 0.5 mg of DNA was mixed with various cytofectins at a 10:1 molar ratio of DNA:cytofectin in 1.5 ml saline Two days after injection of DNA, tumors were collected, extracted, and assayed for CAT activity as described for the intralung assay above.

C. Results

Figure 4:
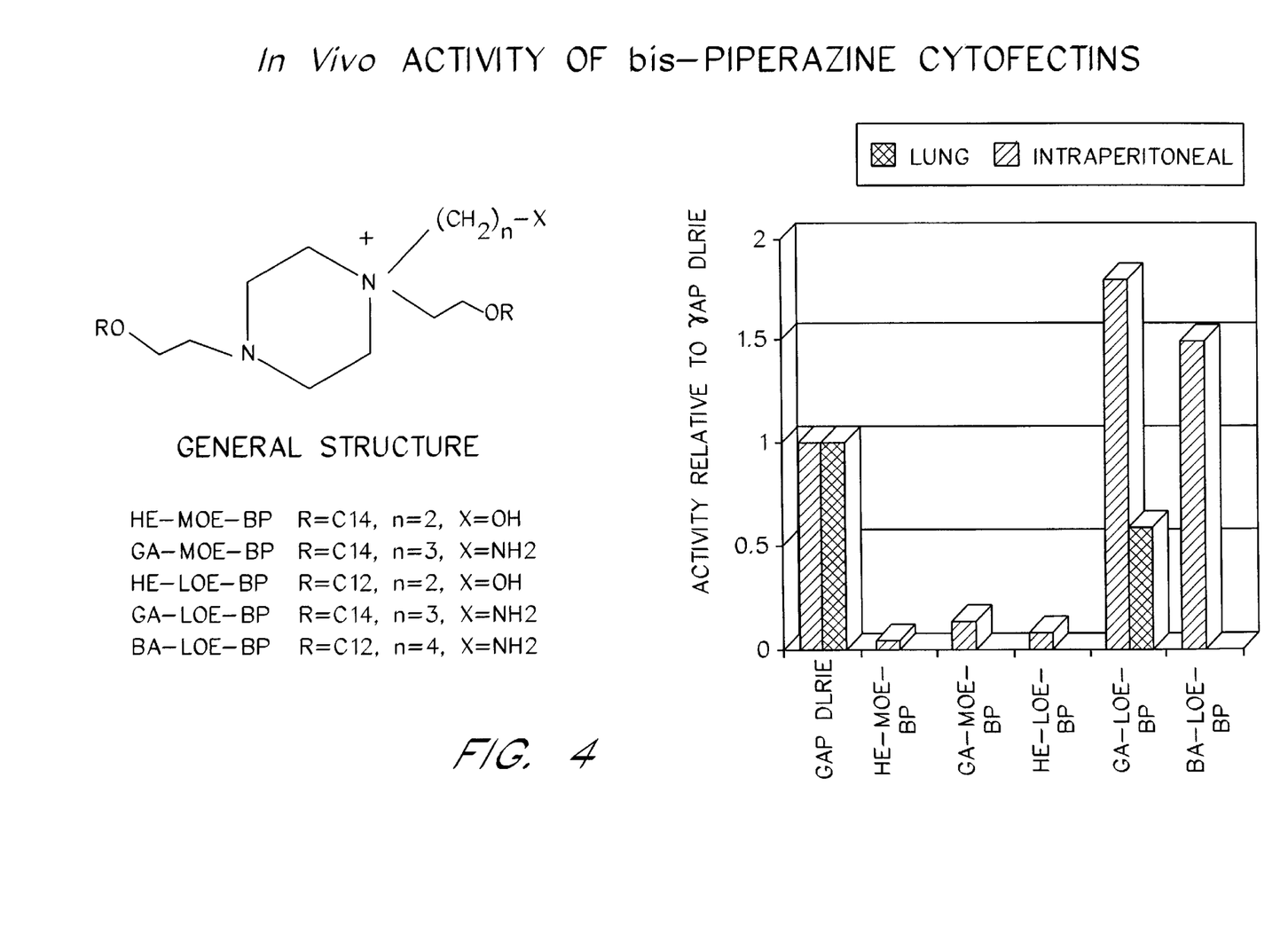
FIG. 4 is an analysis of the transfection efficiencies of several piperazine based cytofectins in the intralung and intraperitoneal transfection assays.

The results obtained with HE-MOE-BP, HE-LOE-BP, GA-MOE-BP, GA-LOE-BP, and BA-LOE-BP in the intralung and intraperitoneal transfection assays are summarized in FIG. 4. In the intralung assay, GA-LOE-BP and BA-LOE-BP provided greater transfection efficiencies than GAP-DLRIE. HE-LOE-BP, GA-MOE-BP, and HE-MOE-BP were less effective in the intralung assay.

In the intraperitoneal assay, GA-LOE-BP provided the greatest transfection efficiency of the piperazine based cytofectins tested, although the transfection efficiency was not as high as that obtained with GAP-DLRIE in this assay. The remaining piperazine based cytofectins which were tested provided little activity in the intraperitoneal assay.

The tests reported here not only indicate that the claimed compounds are active in transfection, but also demonstrate how to select and optimize cytofectins for transfection of particular tissues. Although particular optimum structures are readily apparent for this assay, it will be appreciated that these results are tissue specific; in other words, even cytofectins that performed suboptimally in this assay may have valuable activity in other assays, such as in vitro transfection, murine intraperitoneal tumor, murine intramuscular, porcine or rabbit intraarterial, general subcutaneous tumor, or Renca tumor assays.

EXAMPLE 4

Analysis of Piperazine Based Cytofectins Having Primary Amines

In the DMRIE class of cytofectins, substitution of an alcohol group with a primary amine provided enhanced transfection efficiency. (Wheeler et. al, 1280 *Biochem. Biophys. Acta:* 1–11 (1996)). For this reason, the transfection efficiencies of piperazine based cytofectins having a primary amine joined to a quaternary nitrogen were evaluated relative to the transfection efficiency of DNA alone in the intralung assay. The intralung assay was carried out as in Example 3 above. As a control, the transfection efficiency obtained with 132 µg of DNA alone was determined.

Figure 5:
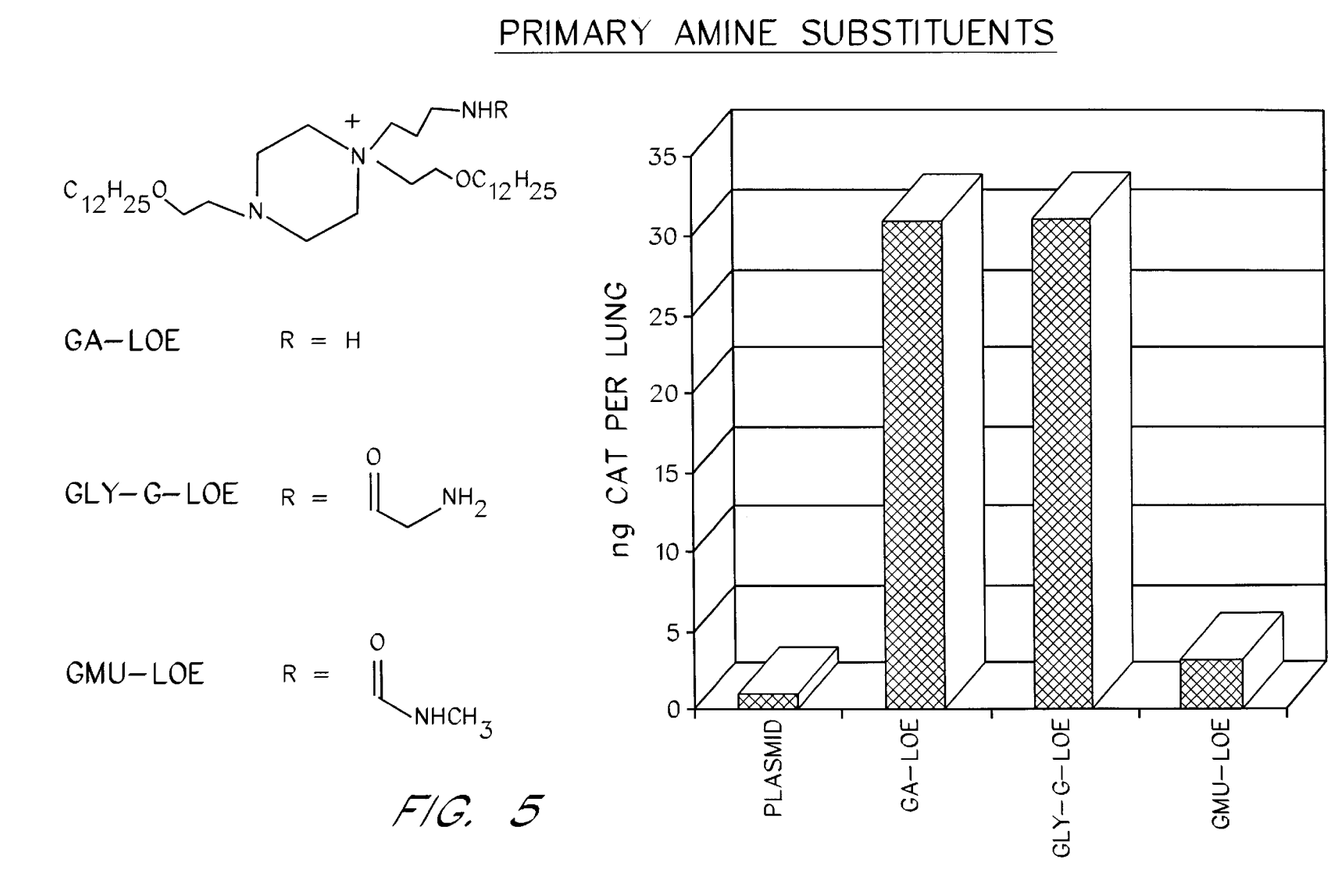
FIG. 5 is an analysis of the transfection efficiencies of several piperazine based cytofectins having primary amines in the intralung transfection assay.

FIG. 5 shows the results of this comparison. Both GA-LOE and Gly-G-LOE, each of which have a primary amine, provided significantly greater transfection levels than DNA alone. The transfection efficiency obtained with GMU-LOE was not as great as that of cytofectins with a primary amine, but was elevated relative to that obtained with DNA alone.

EXAMPLE 5

Figure 6:
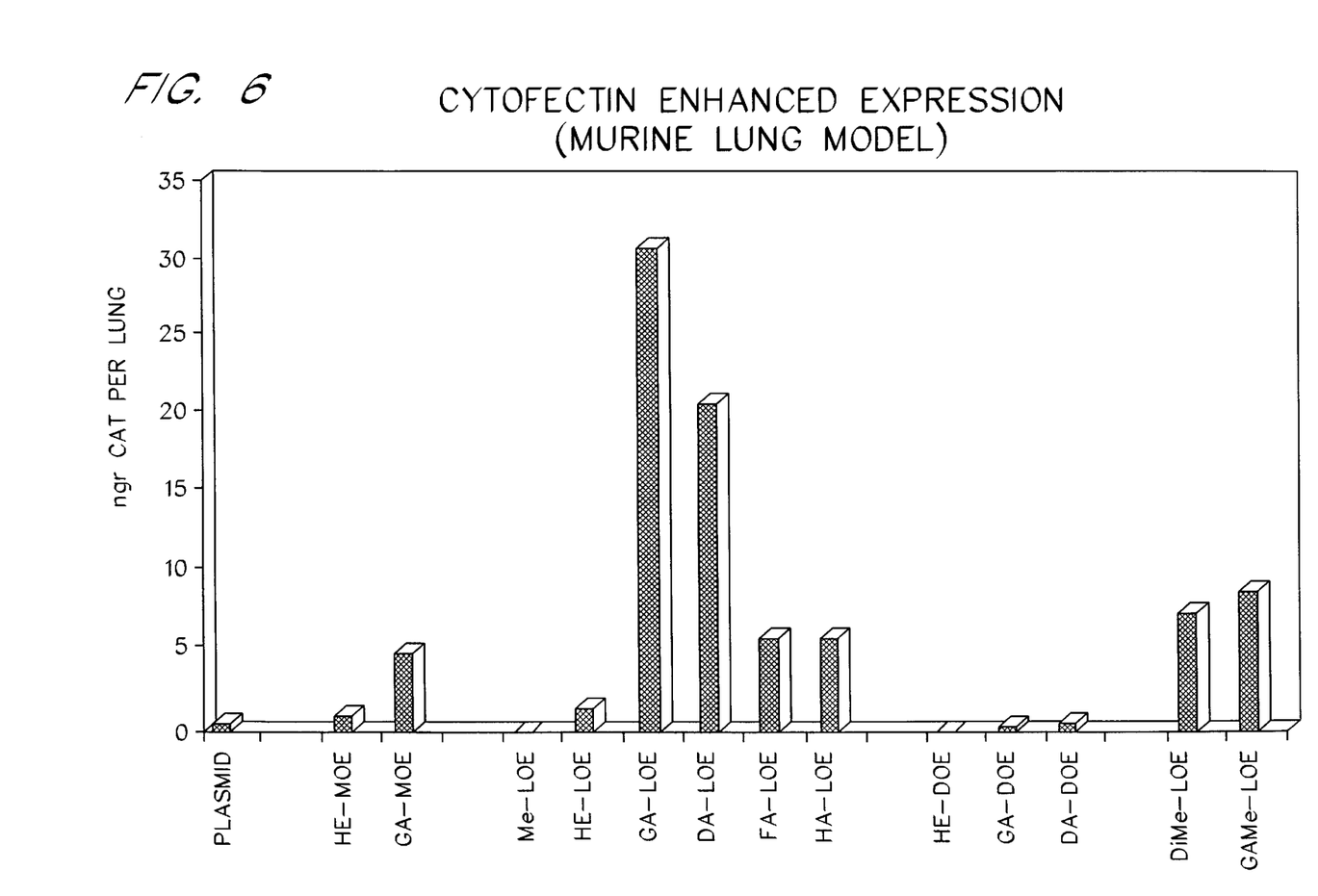
FIG. 6 shows the effect of variation of alkyl chain lengths of the heteroatomic moiety and the lipophilic moiety on transfection efficiency in the intralung transfection assay.

Effect of Variation of Alkyl Chain Lengths of the Heteroatomic Moiety and the Lipophilic Moiety on Transfection Efficiency Transfection efficiencies in different cell types are influenced by the identities of the lipophilic and heteroatomic chain lengths. For this reason, the transfection efficiencies of piperazine based cytofectins differing in the chain lengths of the lipophilic and heteroatomic groups were compared in the intralung assay. The intralung assay was conducted as described in Example 3 above. FIG. 6 shows the results.

Among the piperazine based cytofectins having a primary amine group, the greatest transfection efficiency was obtained with GA-LOE. GA-MOE and GA-DOE, which differ from GA-LOE only in the length of the lipophilic chain, exhibited less activity, although GA-MOE was more effective than DNA alone.

Similarly, as the chain length of the primary amine increased, the transfection efficiency decreased. GA-LOE exhibited greater activity than DA-LOE, while DA-LOE was more efficient than FA-LOE or HA-LOE. All the tested piperazine based cytofectins having a primary amine were more effective than DNA alone.

Among the piperazine based cytofectins having an alcohol group on the heteroatomic moiety, HE-LOE was most effective. However, in the intralung assay, the cytofectins having a primary amine were more efficient than those with an alcohol group.

EXAMPLE 6

General Subcutaneous Tumor Transfection Assay

Tumors are prepared by injecting a suspension of tumor cells subcutaneously on the side of a mouse strain which is compatible with the specific tumor type. The tumors are periodically measured. Once they reached a size suitable for injection, the tumor volume is approximated based on the measured diameter assuming a spherical tumor. A complex of the cytofectin to be evaluated with a plasmid encoding a reporter gene in a volume of saline equal to the volume of the tumor to be treated is then injected at a flow rate optimized for the particular tumor type. After an appropriate time, the tumors are collected, frozen, then ground up. The reporter gene product is subsequently extracted and the activity was quantitated as described above.

EXAMPLE 7

Analysis of Piperazine Based Cytofectins in the Subcutaneous Tumor and Intraperitoneal Transfection Assays The transfection efficiencies of GAP-DLRIE and GA-LOE-BP were measured relative to that of DNA alone in the intraperitoneal and subcutaneous tumor assays The intraperitoneal assay was conducted as described in Example 3. The subcutaneous tumor assay was conducted as described in Example 6 above using murine B16 melanoma cells.

Figure 7:
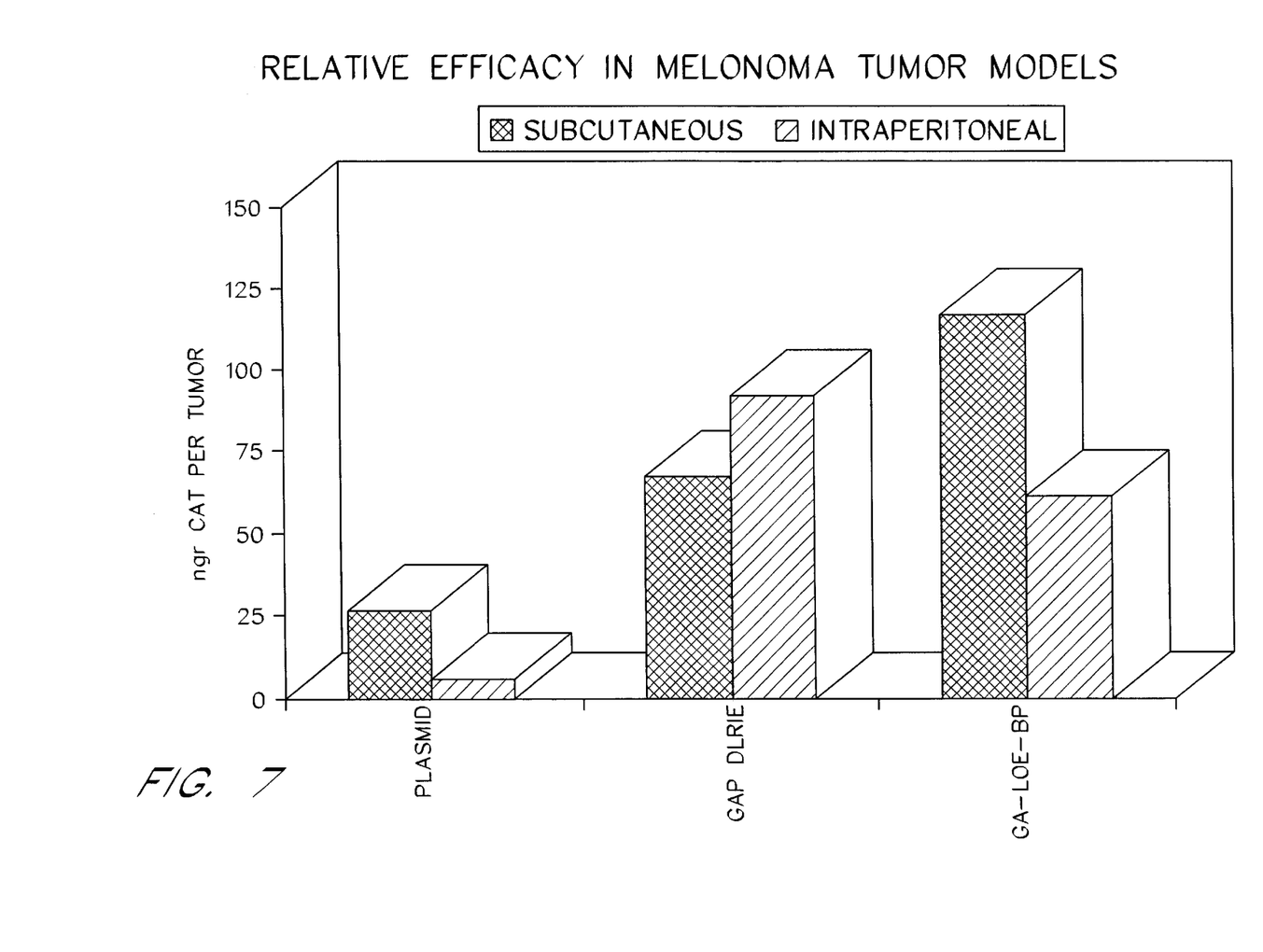
FIG. 7 is a analysis of the transfection efficiencies of GAP-DLRIE and GA-LOE-BP were measured relative to that of DNA alone in the intraperitoneal and subcutaneous tumor assays.

The results are shown in FIG. 7. In the subcutaneous tumor assay, GA-LOE-BP yielded greater transfection efficiency than GAP-DLRIE. The transfection efficiencies observed with both GAP-DLRIE and GA-LOE-BP were greater than that observed with plasmid alone.

In the intraperitoneal assay, GA-LOE-BP was less efficient than GAP-DLRIE but both GA-LOE-BP and GAP-DLRIE increased transfection efficiency relative to plasmid alone.

EXAMPLE 8

Subcutaneous Renca Tumor Model

Renca tumors were propagated in 90% RPMI 1640/10% Fetal Bovine Serum. The tumors are injected subcutaneously into the side of BALB/C mice in 75 $\mu$L of a suspension containing approximately $10^6$ cells/mL tissue culture medium. When the tumors reach 4.5 to 7 mm in diameter the volume of each individual tumor is calculated by measuring the diameter of the tumor and assuming a spherical tumor. For each individual tumor, a volume of the cytofectin/CAT plasmid complex in saline equivalent to the calculated volume of the tumor is injected into the tumor at a rate of 2 mL/min. After 48 hours, the tumors are collected, frozen, ground up, and extracted with 1.5 mL of extraction buffer as described in Example 3. CAT activity is quantitated as described in Example 3.

EXAMPLE 9

Intraarterial Assay

Arterial gene transfer is performed in Yorkshire pigs or rabbits as follows. Arterial gene transfer is performed in the right and left iliofemoral arteries of each pig as described in Nabel, Science 249:1285–1288 (1990). Briefly, after anesthesia, the right and left iliofemoral arteries are exposed by surgical technique, and a double balloon catheter (USCI) is positioned in each artery. The artery is injured by inflating the proximal balloon to 500 mmHg for 1 minute. The catheter is then repositioned for performing gene transfer in the injured region of the artery. The arterial segment is flushed with vector solution consisting of the cytofectin being tested, the vector DNA, and opti-MEM (Gibco/BRL). A mixture of 100 $\mu$g DNA and 300 $\mu$g lipid is instilled. The vector solution is instilled into the site of injury for 20 minutes at 150 mmHg. Following instillation, the catheter is removed and the animal is allowed to recover. Forty eight hours after transfection the arteries are removed. Tissues are crushed using a glass pestle and subsequently freeze thawed three times. Samples are incubated 10 minutes at 65° C. to inactivate endogenous acetylase. Proteins are extracted and their concentration is determined using a colorimetric assay (Bio-Rad, Hercules, Calif.). In each assay 200 $\mu$g of total protein is assayed for CAT activity according to the procedure described above in Example 3 using a four hour incubation period.

EXAMPLE 10

Gene Transfer into Porcine Arteries and Atherosclerotic Rabbit Arteries

Liposome transfection of porcine or rabbit arteries is performed by anesthesia, intubation and sterile exposure of the iliofemoral arteries as described. (Nabel et al., *Science*, 249:1285–1288, 1990). A double balloon catheter is inserted into the iliofemoral artery, and the proximal balloon is inflated to 500 mm Hg for 5 minutes. The balloon is deflated and the catheter is advanced so that the central space between the proximal and distal balloon is irrigated with heparinized saline. The CAT DNA solution (CAT DNA±cytofectin is instilled for 20 minutes in the central space of the catheter. The catheter is removed and antigrade blood flow is restored. Arteries are analyzed two days later for recombinant CAT expression. Arteries transfected with CAT DNA in the presence of cationic lipid exhibit a significant increase in CAT gene expression compared to arteries contacted with the DNA alone.

In vivo gene transfer of atherosclerotic rabbit iliac arteries is performed using a double injury model which is described by Faxon et al. (*Arteriosclerosis*, 4:189–195, 1984). After the second angioplasty injury is completed, the angioplasty balloon is withdrawn slightly so that the end hold infusion port of the catheter is at the proximal end of the injury. A ligature is placed at the distal end of the injury and the injured segment is flushed with heparinized saline and CAT DNA±cationic lipid liposome solution is instilled for 20 minutes into the isolated injured segment. The catheter is removed and antigrade blood flow is restored. Arteries are analyzed two days later for recombinant CAT expression. This assay illustrates another screening assay for optimizing the structure of a particular cytofectin for use in a particular tissue.

EXAMPLE 11

Intramuscular Assay

The quadriceps of restrained, awake mice are injected with 50 $\mu$g luciferase or CAT DNA±cytofectin in 50 $\mu$l USP saline using a disposable sterile, plastic insulin syringe fitted with a 28G ½ needle (Becton-Dickinson) and a plastic collar cut from a yellow Eppendorf micropipette tip. The collar length is adjusted to limit the needle orifice penetration to a distance of about 2 mm into the central part of the 3 mm diameter rectus femoris muscle. Injection fluids and syringes are equilibrated to room temperature and injection of the single 50 μl volume of saline-DNA requires several seconds. The entire quadriceps muscle group (140–180 mg wet weight) is collected from each mouse leg at various times post-injection. Muscles are frozen and lysed as described in Example 3.

Luciferase activity is assayed using an automated microplate luminometer (Dynatech Model ML2250). One hundred μl of luciferase substrate is added by the luminometer's injection system to 20 μl extract and sample light units are recorded. The luciferase content of the samples is calculated from Relative light Units using a standard curve of purified firefly luciferase performed in the presence of uninjected muscle extract. The luciferase activity present in the injected muscle extract is much higher than in the uninjected muscle extract.

This assay illustrates another screening assay for optimizing the structure of a particular cytofectin for use in a particular tissue.

Without further elaboration, it is believed that one skilled in the art can, using the preceding description, utilize the invention to its fullest extent. The invention may be embodied in other specific forms without departing from its spirit of essential characteristics. The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

What is claimed is:

1. A piperazine based cytofectin of the following structure:

wherein $R_1$ and $R_4$ are independently H, linear $C_1$–$C_{23}$ groups, or branched $C_1$–$C_{23}$ groups, said linear or branched $C_1$–$C_{23}$ groups being alkyl, acyl, alkene, or heteroalkyl groups, said alkyl, acyl, alkene or heteroalkyl groups being unsubstituted or substituted, having 0 to 6 sites of unsaturation, containing 0 to 5 heteroatoms, or containing cyclic or aryl groups, said cyclic or aryl groups containing 0–5 heteroatoms;

$R_2$ is a linear $C_1$–$C_{23}$ group, or a branched $C_1$–$C_{23}$ group, said linear or branched $C_1$–$C_{23}$ groups being alkyl, acyl, alkene or heteroalkyl groups, said alkyl, acyl, alkene or heteroalkyl groups being unsubstituted or substituted, having 0 to 6 sites of unsaturation, containing 0 to 5 heteroatoms, or containing cyclic or aryl groups, said cyclic or aryl groups containing 0–5 heteroatoms;

$R_3$ is H, an amino acid, peptide, polypeptide, protein, nucleic acid, nucleotide, nucleoside, polynucleotide, polynucleoside, monosaccharide, disaccharide, polysaccharide, bioactive agent, pharmaceutical agent, a linear $C_1$–$C_{23}$ group, or a branched $C_1$–$C_{23}$ group, said linear or branched $C_1$–$C_{23}$ groups being alkyl, acyl, alkene, or heteroalkyl groups, said alkyl, acyl, alkene or heteroalkyl groups being unsubstituted or substituted, having 0 to 6 sites of unsaturation, containing 0 to 5 heteroatoms, or containing cyclic or aryl groups, said cyclic or aryl groups containing 0–5 heteroatoms, or a group having the following structure:

wherein $R_7$ through $R_{12}$ are independently absent, H, an amino acid, nucleotide, polynucleotide, monosaccharide, disaccharide, polysaccharide, bioactive agent, pharmaceutical agent, linear $C_1$–$C_{23}$ groups, or branched $C_1$–$C_{23}$ groups, said linear or branched $C_1$–$C_{23}$ groups being alkyl, acyl, alkene or heteroalkyl groups, said alkyl, acyl, alkene or heteroalkyl groups being unsubstituted or substituted, having 0 to 6 sites of unsaturation, containing 0 to 5 heteroatoms, or containing cyclic or aryl groups, said cyclic or aryl groups containing 0 to 5 heteroatoms;

G is absent, O, N, NH, S, SH, Se, C, CH, or $CR_1$;

T is O, N, S, Se, or C;

A is O, N, S, Se, or C;

$Y_1$ and $Y_2$ are independently O, N, NH, S, or Se;

$X_1$ is O or NH;

m and p are independently 1–6;

W is a pharmaceutically acceptable anion.

2. The piperazine based cytofectins of claim 1 wherein m and p are 2.

3. The piperazine based cytofectins of claim 2 wherein $Y_1$ and $Y_2$ are O.

4. The piperazine based cytofectins of claim 3 wherein $R_1$ and $R_4$ are selected from the group consisting of $C_{10}H_{21}$, $C_{12}H_{25}$, and $C_{14}H_{29}$.

5. The piperazine based cytofectins of claim 4 wherein $R_2$ is selected from the group consisting of absent, $CH_2$, $(CH_2)_2$, $(CH_2)_3$, $(CH_2)_4$, $(CH_2)_5$, $(CH_2)_6$.

6. A piperazine based cytofectin of the following structure:

wherein $R_1$, $R_2$, $R_4$, and $R_5$ are independently H, linear $C_1$–$C_{23}$ groups, or branched $C_1$–$C_{23}$ groups, said linear or branched $C_1$–$C_{23}$ groups being alkyl, acyl, alkene or heteroalkyl groups, said alkyl, acyl, alkene, or heteroalkyl groups being unsubstituted or substituted, having 0 to 6 sites of unsaturation, containing 0 to 5 heteroatoms, or containing cyclic or aryl groups, said cyclic or aryl groups containing 0–5 heteroatoms;

$R_3$ and $R_6$ are each independently H, an amino acid, peptide, polypeptide, protein, nucleic acid, nucleotide, nucleoside, polynucleotide, polynucleoside, monosaccharide, disaccharide, polysaccharide, bioactive agent, pharmaceutical agent, a linear $C_1$–$C_{23}$ group, or a branched $C_1$–$C_{23}$ group, said linear or branched $C_1$–$C_{23}$ groups being alkyl, acyl, alkene or heteroalkyl groups, said alkyl, acyl, alkene or heteroalkyl groups being unsubstituted or substituted, having 0 to 6 sites of unsaturation, containing 0 to 5 heteroatoms, or containing cyclic or aryl groups, said cyclic or aryl groups containing 0–5 heteroatoms, or a group having the following structure:

wherein $R_7$ through $R_{12}$ are independently absent, H, an amino acid, nucleotide, polynucleotide, monosaccharide, disaccharide, polysaccharide, bioactive agent, pharmaceutical agent, linear $C_1$–$C_{23}$ groups, or branched $C_1$–$C_{23}$ groups, said linear or branched $C_1$–$C_{23}$ groups being alkyl, acyl, alkene, or heteroalkyl groups, said alkyl, acyl, alkene, or heteroalkyl groups being substituted or unsubstituted, having 0 to 6 sites of unsaturation, containing from 0 to 5 heteroatoms, or containing cyclic or aryl groups, said cyclic or aryl groups containing 0 to 5 heteroatoms;

G is absent, O, N, NH, S, SH, Se, C, CH, or $CR_1$;

T is O, N, S, Se, or C;

A is O, N, S, Se, or C;

$Y_1$ and $Y_2$ are independently O, N, NH, S, or Se;

$X_1$ and $X_2$ are independently selected from the group consisting of absent, O, and NH;

m and p are independently 1–6;

W is a pharmaceutically acceptable anion; and wherein either $X_1$ or $X_2$ is present or both $X_1$ and $X_2$ are present.

7. The piperazine based cytofectins of claim 6, wherein both $X_1$ and $X_2$ are present.

8. The piperazine based cytofectins of claim 6, wherein either $X_1$ or $X_2$ but not both is present.

9. The piperazine based cytofectins of claim 6 wherein m and p are 2.

10. The piperazine based cytofectins of claim 9 wherein $Y_1$ and $Y_2$ are O.

11. The piperazine based cytofectins of claim 10, wherein $R_5$ and $R_2$ are selected from the group consisting of absent, $CH_2$, $(CH_2)_2$, $(CH_2)_3$, $(CH_2)_4$, $(CH_2)_5$ and $(CH_2)_6$.

12. The piperazine based cytofectins of claim 11 wherein $R_1$ and $R_4$ are selected from the group consisting of $C_{10}H_{21}$, $C_{12}H_{25}$, and $C_{14}H_{29}$.

13. A method of deleivering a molecule into a cell comprising the steps of:

(a) contacting the moleucle with an effective amount of a cytofectin according to claim 1 to form a complex with the cytofectin; and (b) contacting the cell with the complex formed in step (a) whereby said molecule is delivered into said cell.

14. The method of claim 13, wherein said molecule is an anionic molecule.

15. The method of claim 14, wherein said anionic molecule is selected from the group consisting of mRNA and DNA.

16. The method of claim 13, wherein said complex includes one or more lipids in addition to said cytofectins of claim 1.

17. The method of claim 16, wherein said lipids are selected from the group consisting of neutral lipids, phospholipids and cholesterol.

18. A method of deleivering a molecule into a cell comprising the steps of:

(a) contacting the moleucle with an effective amount of a cytofectin according to claim 6 to form a complex with the cytofectin; and (b) contacting the cell with the complex formed in step (a) whereby said molecule is delivered into said cell.

19. The method of claim 18, wherein said molecule is an anionic molecule.

20. The method of claim 19, wherein said anionic molecule is selected from the group consisting of mRNA and DNA.

21. The method of claim 18, wherein said complex includes one or more lipids in addition to said cytofectins of claim 1.

22. The method of claim 21, wherein said lipids are selected from the group consisting of neutral lipids, phospholipids and cholesterol.

* * * * *